United States Patent [19]

Hewlins et al.

[11] Patent Number: 5,124,254
[45] Date of Patent: Jun. 23, 1992

[54] DETECTION OF DIAMINES IN BIOLOGICAL FLUIDS

[75] Inventors: Michael J. E. Hewlins, Penylan; Thomas C. O'Dowd, Woodborough; Robert H. Davis, Corntown; Peter J. Winterburn, Cyncoed, all of United Kingdom

[73] Assignees: University College Cardiff Consultants Limited; Welsh Medical School Enterprises Limited, Cardiff, England

[21] Appl. No.: 555,412

[22] PCT Filed: Feb. 8, 1989

[86] PCT No.: PCT/GB89/00191

§ 371 Date: Oct. 2, 1990

§ 102(e) Date: Oct. 2, 1990

[87] PCT Pub. No.: WO89/07152

PCT Pub. Date: Aug. 10, 1989

[30] Foreign Application Priority Data

Feb. 8, 1988 [GB] United Kingdom ............... 8802821
Mar. 1, 1988 [GB] United Kingdom ............... 8804838

[51] Int. Cl.$^5$ .................... C12Q 1/28; C12Q 1/26; C12Q 1/02; C12Q 1/16
[52] U.S. Cl. ......................... 435/28; 435/25; 435/29; 435/34
[58] Field of Search ............... 435/29, 34, 25, 28

[56] References Cited

U.S. PATENT DOCUMENTS 4,550,078 10/1985 Yamada et al. ............... 435/25
4,617,263 10/1986 Yamada et al. ............... 435/25

FOREIGN PATENT DOCUMENTS 61-274698 5/1985 Japan .

OTHER PUBLICATIONS

Chen et al. (1979) Amine Content of Vaginal Fluid ... J. Clin. Invest. 63: 828–835.
Jawetz et al. (1987) Review of Microbiology Appleton & Lang, p. 278.
Bergmeyer et al. (1985) Methods of Enzymatic Analysis Verlag-Chemi, pp. 566–568.
Biondi et al. (1984) Chem. Abstracts 101:125482o.
Davis (1980) In: Daus et al. Microbiology 3rd Ed. pp. 53–54, Harper & Row, Philadelphia.
Matsumoto et al. (1981) A Fluorometric Assay for Diamines in ... urine ... Clin. Chimica ACTA, 112:141-8.
Bergmeyer et al. (1985) In. Methods of Enzyme Analysis. VCH (Weinheim, DE) pp. 566–568.
"A Sensitive, Rapid, Chemiluminescence-Based Method for the Determination of Diamines and Polyamines", Uriel Bachrach et al., Analytical Biochemistry, 152, 423–431 (1986).
"A Fluorometric Assay for Total Diamines in Human Urine Using Human Placental Diamines Oxidase", T. Matsumoto et al., Clinica Chimica ACTA, 112, 141–148 (1981).

Primary Examiner—Christine Nucker
Assistant Examiner—David R. Preston
Attorney, Agent, or Firm—Weingarten, Schurgin, Gagnebin & Hayes

[57] ABSTRACT

A fast-acting and portable diagnostic kit for detecting diamines in biological fluids is in the form of a diamine oxidase and a chromogenic system to detect the presence of hydrogen peroxide resulting from oxidation of such diamines. The kit may especially be used to detect cadaverine or putrescine or a mixture thereof, for example in a vaginal secretion, in order to detect Gardnerella-related bacterial vaginosis.

15 Claims, No Drawings

DETECTION OF DIAMINES IN BIOLOGICAL FLUIDS

This invention relates to a method for the identification of diamines, particularly putrescine and cadaverine in vaginal secretions, and the use of this in diagnosis of a certain clinical condition, and to a diagnostic kit to enable the method to be applied routinely.

Vaginitis is a widespread problem in general practice. One common form of vaginitis was characterised by Gardner and Dukes (H. L. Gardner and C. D. Dukes, Am. J. Obstet. Gynecol., 1955, 69, 962–976) who described a condition associated with a grey homogeneous discharge having a pH of 5.0–5.5 and accompanied by minimal inflammation. The condition appears to be associated with the organism *Gardnerella vaginalis* in the presence of other organisms, notably anaerobic bacteria. This form of vaginitis is now often called bacterial vaginosis to acknowledge the complexity of its microbiological origin.

Clinical diagnosis of this condition is aided by identification of "clue cells" (vaginal epithelial cells with adherent surface bacteria), a raised pH, and a "fishy" odour generated on adding alkali to the secretion (the "amine" test) (H. L. Gardner and C. D. Dukes, loc. cit.; T. Pheifer et al., New Eng. J. Med., 1978, 298, 1429–1434; R. Amsel et al., Am. J. Med., 1983, 74, 14–22; Report of The Working Group on "The Diagnosis of Bacterial Vaginosis", Scand. J. Urol. Nephrol. (Suppl.), 1984, 86, 260–261).

Microbiological confirmation of *G. vaginalis* is not straightforward and culture results take 2–3 days. There is no simple, rapid, diagnostic procedure. It is known that the diamines putrescine and cadaverine occur at significantly elevated levels in Gardnerella-related vaginitis (K. C. S. Chen et al., J. Clin. Invest., 1979, 63, 828–835); these diamines are probably produced by the symbiotic growth of *G. vaginalis* in the presence of the anaerobes. Earlier work showed that the presence of the diamines correlated with clinical symptoms in 96% of patients (K. C. S. Chen et al., J. Infect. Dis. 1982, 145, 337–345).

Previously the detection of the diamines has depended on electrophoresis or thin-layer chromatography (K. C. S. Chen et al., loc. cit.) requiring specialist equipment and personnel. The aim of this invention is to provide a method to establish the presence of the diamines in a way that can be carried out in a laboratory, clinic, surgery, or in the home, by persons not skilled in chemical analysis or microbiological procedures.

The invention uses a selected diamine oxidase which reacts with the diamines, putrescine and cadaverine, to give hydrogen peroxide. This is detected by a colour reaction produced by peroxidase and a suitable chromogenic system. A suitable diamine oxidase (E. C. 1.4.3.6) can be isolated from pea seedlings (R. E. McGowan and R. M. Muir, Plant Physiol., 1971, 47, 644–649); this oxidises putrescine and cadaverine with a high specificity. Other diamine oxidases, for example that from pig kidney(Sigma Chemical Co.), can be used in a similar way. Peroxidase is a well-known enzyme that is commercially available. For the chromogenic system, a number of different reagents may be used. A mixture of 4-aminoantipyrine and 3,5-dichloro-2-hydroxybenzenesulphonic acid, introduced by Barham and Trinder (D. Barham and P. Trinder, Analyst, 1972, 97, 142–145) to detect hydrogen peroxide, proves very satisfactory, but other phenolic components, for example chromotropic acid or 2,4,6-tribromo-3-hydroxybenzoic acid, may also be used satisfactorily. Other chromogenic systems which also work successfully include 3,3',5,5'-tetramethylbenzidine and 2,2'-azino-bis-(3-ethylbenzthiazoline-6-sulphonate).

The diagnostic test in its first form involves taking a vaginal swab and agitating it in a solution containing the diamine oxidase, peroxidase, and the chromogenic compounds. When a mixture of 4-aminoantipyrine and 3,5-dichloro-2-hydroxybenzenesulphonic acid is used as the chromogenic system, the positive magenta colour develops in under two minutes and is stable for more than one hour. Quantitative measurement can be obtained from the optical density of the solution, but this is not necessary for the clinical diagnostic test. Negative samples give no colour, or at most a very pale colour. The solution of reagents for the test in this form can be made by simple addition of water to a freeze-dried mixture of all the ingredients prepared in a suitable vessel. This freeze-dried mixture can be stored without deterioration of its efficiency. Alternatively the reagents can be constituted in other ways, for example in a tablet form or adsorbed on to paper to other surface layer.

Clinical samples of 183 vaginal secretions have been tested and the results correlated with existing diagnostic procedures-the "amine" test, "clue cells" and culture of *G. vaginalis*. These correlations, and the sensitivities and specificities, are presented in Example 7 (see below). The diamine test results correlate closely with the microbiological culture and with the two sideroom techniques; "clue cell" and "amine" tests. The agreements in the comparisons with "clue cells" and the "amine" test are marginally better than those with the microbiological results from the Public Health Laboratory Service. In all three comparisons the diamine test gave slightly poorer apparent specificity than sensitivity. Thus, sensitivity for microbiological, "clue cell" and "amine" tests was 86%, 96% and 93% respectively. The new test thus works well as a diagnostic procedure.

EXAMPLES

EXAMPLE 1

Linearity of Response of the Diamine Oxidase/Dye System to Increasing Concentrations of Putrescine Procedure Each incubation contained the following reagents:
4-aminoantipyrine (5 mg/ml; 0.1 ml);
3,5-dichloro-2-hydroxy-benzenesulphonic acid (35 mg/ml; 0.1 ml);
peroxidase (1 mg/ml; 0.1 ml);
diamine oxidase (5–15 units/ml; 0.02 ml);
putrescine (0–1.25 mM; 0.1 ml);
buffer (0.1M tris-HCl, pH 7.5; 2 ml).

The reagents were mixed and the absorbance at 515 nm was recorded after a 10 minute incubation. The absorbance was proportional to the amount of putrescine added, so establishing that the relationship between absorbance and the quantity of putrescine in the assay was linear over the range studied (0–125 nmol putrescine per assay).

TABLE

| nmol putrescine | A 515 nm | nmol putrescine | A 515 nm |
| --- | --- | --- | --- |
| 0 | 0 | 25 | 0.292 |
| 1 | 0.012 | 50 | 0.584 |
| 2.5 | 0.028 | 75 | 0.885 |

TABLE-continued

| nmol putrescine | A 515 nm | nmol putrescine | A 515 nm |
| --- | --- | --- | --- |
| 5 | 0.058 | 100 | 1.160 |
| 7.5 | 0.088 | 125 | 1.446 |
| 10 | 0.113 | | |

EXAMPLE 2

Additivity of the Response of the Diamine Oxidase/Dye System to the Two Diamines, Putrescine and Cadaverine The procedure was as described in Example 1, but using either putrescine or cadaverine, or mixtures of both putrescine and cadaverine. Putrescine and cadaverine gave similar absorbances on a molar basis and when present together in the incubation the absorbance produced was that predicted by a simple addition of the absorbances given by the two diamines separately.

TABLE

| | Absorbance 515 nm | | | |
| --- | --- | --- | --- | --- |
| Substrate concentration of each diamine | column 1 putrescine alone | column 2 cadaverine alone | column 3 mixture of putrescine + cadaverine | column 4 column 1 + column 2 |
| 1 nmol | 0.011 | 0.009 | 0.018 | 0.020 |
| 10 nmol | 0.113 | 0.096 | 0.225 | 0.209 |
| 100 nmol | 1.105 | 1.104 | 2.163 | 2.209 |

(Column 4 is calculated as the addition of the absorbances in columns 1 and 2.)

EXAMPLE 3

Response of the Diamine Oxidase/Dye System to Other Amines or Diamines

The procedure was as described in Example 1, but the putrescine was replaced by other biologically important amines. The other amines included: alanine, asparagine, aspartic acid, arginine, cysteine, cystine, glutamic acid, glutamine, glycine, histidine, isoleucine, leucine, lysine, methionine, ornithine, phenylalanine, proline, serine, threonine, tyrosine, tryptophan, valine, 4-aminobutyric acid, histamine, phenethylamine, spermine and tyramine. Colour production was not detectable, or was slight or very slow to develop with these other amines. Thus, the response of the diamine oxidase/dye system to these biologically important amines that may be present in secretions or fluids could be readily distinguished from the colour production by putrescine and cadaverine.

EXAMPLE 4

Alternative Dye Systems Used in Conjunction with the Diamine Oxidase

The procedure was as described in Example 1, except that the incubation contained 2,2'-azino-bis-(3-ethyl-benzthiazoline-6-sulphonate) (14 mg/ml; 0.1 ml) instead of 4-aminoantipyrine and 3,5-dichloro-2-hydroxybenzenesulphonic acid. The absorbance was measured at 646 nm after an incubation at room temperature for 60 minutes.

TABLE

| nmol putrescine | A 646 nm | nmol putrescine | A 646 nm |
| --- | --- | --- | --- |
| 0 | 0 | 25 | 0.172 |
| 1 | 0.008 | 50 | 0.336 |
| 2.5 | 0.018 | 75 | 0.490 |
| 5 | 0.035 | 100 | 0.643 |
| 7.5 | 0.054 | 125 | 0.801 |

TABLE-continued

| nmol putrescine | A 646 nm | nmol putrescine | A 646 nm |
| --- | --- | --- | --- |
| 10 | 0.070 | | |

This alternative dye system gave absorbances proportional to the putrescine concentration and thus demonstrated that the procedure was not dependent on the dye system quoted in Example 1 but would operate with other hydrogen peroxide detection systems.

EXAMPLE 5

Stability of the Reagents in a Dried Form

Transparent polystyrene tubes were prepared containing in freeze-dried form the following components:
4-aminoantipyrine (0.5 mg);
3,5-dichloro-2-hydroxybenzenesulphonic acid (3.5 mg);
peroxidase (0.1 mg);
diamine oxidase (0.2 units);
tris-HCl, pH 7.5 (0.2 mmol).

This freeze-dried mixture contained the same amounts of the reagents as in Example 1, with the omission of putrescine.

Each tube was reconstituted with 2.3 ml water after 6 weeks storage at 4° C. and the reactivity compared with a fresh solution of the same composition. Putrescine (50 nmol) was added to each test (in triplicate) and the absorbances compared.

TABLE

| | Absorbances 515 nm | | | |
| --- | --- | --- | --- | --- |
| | | | | mean |
| Fresh | 0.588 | 0.587 | 0.612 | 0.596 |
| Reconstituted | 0.608 | 0.607 | 0.609 | 0.608 |

Thus, when the components were stored in a dried form there was no loss of reactivity by the diamine oxidase/dye system. Similarly, when the same components were dried on to a strip of Whatman No. 1 chromatography paper and the paper dipped into a solution containing putrescine, a magenta colour developed.

EXAMPLE 6

Application of the Diamine Oxidase/Dye System to the Analysis of Diamines in Vaginal Secretions Vaginal swabs were taken from:
(i) patients consulting for vaginitis,
(ii) patients consulting for cervical smears or family planning advice,
(iii) women invited to health checks.

Each swab was washed twice with 1 ml 0.1M-tris/HCl buffer, pH7.5. Any particulate material in the combined washings was removed by brief centrifugation and/or filtration. An aliquot (0.5 ml) was added to a mixture containing:
tris/HCl buffer(pH7.5, 0.1M, 1.5 ml);

3,5-dichloro-2-hydroxybenzenesulphonic acid (35 mg/ml; 0.1 ml);
4-aminoantipyrine (5 mg/ml; 0.1 ml);
peroxidase (1 mg/ml; 0.1 ml);
diamine oxidase (10 units/ml, 0.02 ml).

The absorbance at 515 nm was measured after a 10 minute incubation at room temperature and the amount of diamine calculated from a standard calibration. From a survey of 183 swabs the amount of diamine in each swab was estimated. The range of values was found to be 0-540 nmol diamines/swab.

EXAMPLE 7

183 vaginal swabs were assayed quantitatively by the procedure described in Example 6 and the results compared with the microbiological culture by the Public Health Laboratory Service and with current sideroom methods of diagnosing Gardnerella-related vaginitis. Details of the "amine" test, identification of "clue" cells and of the taking, storing, transporting and cultures of swabs at the Public Health Laboratory Service have been described (T.C.O'Dowd et al., J. Roy. Coll. Gen. Pract., 1987, 37, 59-61).

Microbiological Comparison

The Public Health Laboratory Service identified 57 swabs as *Gardnerella vaginalis* positive and the remaining 126 swabs as *Gardnerella vaginalis* negative. The mean quantity of diamine measured per swab for the Gardnerella positive group was 161 nmol diamines (+146 nmol s.d.) and for the Gardnerella negative group was 37 nmol diamines (+86 nmol s.d.). The difference was statistically highly significant.

If a cut-off at 25 nmol diamines/swab is chosen as the dividing line between a positive and a negative result in the diamine oxidase/dye system assay, the sensitivity of the diamine test was 49/57=86%, i.e. 8 apparent "false negatives", and the specificity of the diamine test was 100/126=79%, i.e. 26 apparent "false positives".

"Clue Cell" Comparison 171 swabs were evaluated for "clue cells". 52 swabs were described as "clue cell positive", 17 swabs as "clue cell uncertain" and 102 swabs as "clue cell negative". The results of the diamine test were 200 nmol diamines (+141 nmol s.d.)/swab, 54 nmol diamines (+103 nmol s.d.)/swab and 22 nmol diamines (+60 nmol s.d.)/swab for the three groups respectively. The statistical evaluation of the three groups revealed that the samples from the "clue cell uncertain" group were statistically different from those of the "clue cell positive" group but not from those of the "clue cell negative" group. Thus, the "clue cell uncertain" and "clue cell negative" groups were considered as constituting a single group.

If a cut-off at 25 nmol diamines/swab is chosen as the dividing line between a positive and a negative result in the diamine oxidase/dye system assay, the sensitivity of the diamine test was 50/52=96%, i.e. 2 apparent "false negatives", and the specificity was 97/119=82%, i.e. 22 apparent "false positives".

"Amine" Test Comparison

Using the same cut-off value of 25 nmol diamines/swab in the diamine oxidase/dye system assay, 40 of 42 swabs judged positive in the "amine" test were also positive by the diamine test. Similarly, 13 of 15 swabs judged possibly positive in the "amine" test and 14 of 87 swabs judged negative for "amines" gave a positive result in the diamine test. If those swabs considered possibly positive are grouped with the positives, the relative sensitivity was 53/57=93%, i.e. 4 apparent "false negatives", and the relative specificity 73/87=84%, i.e. 14 apparent "false positives".

The diamine oxidase/dye system results agreed well with the microbiological culture and with the two sideroom techniques; "clue cell" and "amine" tests. It is apparent that agreements in the comparisons with "clue cells" and the "amine" test are marginally better than those with the microbiological results from the Public Health Laboratory Service.

In all three comparisons the diamine test gave slightly poorer apparent specificity, an indication of "false positives", than sensitivity, an indication of "false negatives". Thus, sensitivity for microbiological, "clue cell" and "amine" tests was 86%, 96% and 93% respectively, whereas the incidence of "false positives" was 21%, 18% and 16% for the microbiological, "clue cell" and "amine" tests respectively. The close agreement with the "amine" test might be expected because the diamine test measures the diamines that create the characteristic odour associated with this sideroom test.

In each of these comparisons the efficiency of the diamine assay is being assessed on the basis that the true answer is given by either the microbiological culture or a sideroom test. However, no single test is currently recognised as a definitive test and diagnosis resides on a collective evaluation of the several tests employed in the comparisons presented here. Thus, the evaluation of the diamine oxidase/dye system assay indicates that it is as accurate as other recognised procedures, but has the advantages of portability and speed, and may be performed by unskilled, untrained personnel or by the patient.

EXAMPLE 8

Application of the Diamine Oxidase/Dye System to the Analysis of Diamines in the Presence of Human Serum Procedure Each incubation contained the following reagents:
4-aminoantipyrine (5 mg/ml; 0.1 ml);
3,5-dichloro-2-hydroxy-benzenesulphonic acid (35 mg/ml; 0.1 ml);
peroxidase (1 mg/ml; 0.1 ml);
diamine oxidase (5-15 units/ml; 0.02 ml);
putrescine or cadaverine (0, 10, 50 or 100 nmol; 0.1 ml);
human serum or buffer (0.1M tris-HCl, pH 7.5; 0.5 ml);
buffer (0.1M tris-HCl, pH 7.5) to make a final volume of 2.1 ml.

The reagents were mixed and the absorbance at 515 nm was recorded after a 10 minute incubation. The absorbance was proportional to the amount of putrescine or cadaverine added, so establishing that the relationship between absorbance and the quantity of either putrescine or cadaverine in the assay was linear in the presence of human serum over the range studied (0-100 nmol diamine per assay).

TABLE

| | (undialysed serum) | | | | |
|---|---|---|---|---|---|
| putrescine | A 515 nm | | cadaverine | A 515 nm | |
| nmol | −serum | +serum | nmol | −serum | +serum |
| 10 | 0.111 | 0.091 | 10 | 0.127 | 0.096 |
| 50 | 0.562 | 0.425 | 50 | 0.616 | 0.503 |
| 100 | 1.118 | 0.948 | 100 | 1.265 | 1.078 |

The presence of serum in the assay reduced the absorbance by 15-20%; this decrease in colour formation was the same for both putrescine and cadaverine.

Two similar series of incubations were established, one using human serum that had been dialysed at 4° C. for 24 hours against physiological saline (0.154M-NaCl), and the other using putrescine and cadaverine in the same incubation.

TABLE

| putrescine | (dialysed serum) | | cadaverine | | |
|---|---|---|---|---|---|
| | A 515 nm | | | A 515 nm | |
| nmol | −serum | +serum | nmol | −serum | +serum |
| 10 | 0.111 | 0.089 | 10 | 0.127 | 0.104 |
| 50 | 0.562 | 0.480 | 50 | 0.616 | 0.544 |
| 100 | 1.118 | 0.947 | 100 | 1.265 | 1.096 |

The presence of dialysed serum in the assay had a similar effect to that exhibited by undialysed serum and the decrease in colour formation was the same for both putrescine and cadaverine.

In a similar manner of the findings reported in Example 2, colour formation from putrescine and cadaverine was additive in the presence of either dialysed or undialysed serum.

We claim:

1. A method for the detection of putrescine and cadaverine in vaginal secretions to diagnose vaginal infection comprising the steps of:
    adding a sample of vaginal fluid to a mixture comprising:
    a diamine oxidase having a high specificity for a diamine selected from the group consisting of putrescine and cadaverine, and which reacts with putrescine and cadaverine to form hydrogen peroxide; and
    a chromogenic system to detect the presence of elevated levels of hydrogen peroxide resulting from the reaction between said diamine oxidase and putrescine and cadaverine.

2. A method according to claim 1, wherein the sample is obtained by a swab.

3. A method according to claim 1, wherein the diamine oxidase is derived from pea seedlings.

4. A method according to claim 1, wherein the chromogenic system is composed of peroxidase, 4-aminoantipyrine, and a phenolic compound.

5. A method according to claim 4, wherein the phenolic compound is 3,5-dichloro-2-hydroxybenzenesulphonic acid.

6. A method according to claim 1, wherein the vaginal infection is Gardnerella-related bacterial vaginosis.

7. A diagnostic kit useful for the direct testing of vaginal fluid to detect the presence of elevated levels of putrescine and cadaverine for diagnosis of vaginal infection, consisting essentially of the following elements in at least one container:
    a premeasured amount of diamine oxidase which is highly specific for a diamine selected from the group consisting of putrescine and cadaverine, and which reacts with putrescine and cadaverine to form hydrogen peroxide;
    a premeasured amount of a chromogenic system responsive to hydrogen peroxide;
    said diamine oxidase and said chromogenic system being disposed in said at least one container container.

8. The kit of claim 7 wherein said diamine oxidase and said chromogenic system are in freeze dried form.

9. The kit of claim 7 wherein said diamine oxidase is derived from pea seedlings.

10. The kit of claim 7 wherein said chromogenic system comprises peroxidase, 4-aminoantipyrine and a phenolic compound.

11. The kit of claim 10 wherein the phenolic compound is 3,5-dichloro-2-hydroxybenzenesulphonic acid.

12. A diagnostic device useful for the direct testing of vaginal fluid to detect the presence of elevated levels of putrescine and cadaverine for diagnosis of vaginal infection, consisting essentially of a paper or other surface layer absorbed with a test composition consisting essentially of a premeasured amount of diamine oxidase which is highly specific for a diamine selected from the group consisting of putrescine and cadaverine, and which reacts with putrescine and cadaverine to form hydrogen peroxide, and a premeasured amount of a chromogenic system responsive to hydrogen peroxide.

13. The device of claim 12 wherein said diamine oxidase is derived from pea seedlings.

14. The device of claim 12 wherein said chromogenic system comprises peroxidase, 4-aminoantipyrine and a phenolic compound.

15. The device of claim 14 wherein said phenolic compound is 3,5-dichloro-2-hydroxybenzenesulphonic acid.

* * * * *